(12) United States Patent
Perez-Cruet et al.

(10) Patent No.: US 7,758,556 B2
(45) Date of Patent: Jul. 20, 2010

(54) DEVICE FOR COLLECTING BONE MATERIAL DURING A SURGICAL PROCEDURE

(76) Inventors: Miguelangelo J. Perez-Cruet, 1070 Timberlake Dr., Bloomfield, MI (US) 48302; John R. Pepper, 224 Beacon Hill Dr., Cheshire, CT (US) 06410; John A. Miller, 600 Waddington, Bloomfield Village, MI (US) 48301

( * ) Notice: Subject to any disclaimer, the term of this patent is extended or adjusted under 35 U.S.C. 154(b) by 963 days.

(21) Appl. No.: 11/500,654

(22) Filed: Aug. 8, 2006

(65) Prior Publication Data

US 2007/0225665 A1 Sep. 27, 2007

Related U.S. Application Data

(60) Provisional application No. 60/785,060, filed on Mar. 23, 2006.

(51) Int. Cl.
*A61M 1/00* (2006.01)
(52) U.S. Cl. ...................... 604/317; 604/416
(58) Field of Classification Search ............. 604/317, 604/323, 326–327, 403, 406, 416
See application file for complete search history.

(56) References Cited

U.S. PATENT DOCUMENTS

| | | | |
|---|---|---|---|
| 5,354,262 A | 10/1994 | Boehringer et al. | |
| 5,435,645 A * | 7/1995 | Faccioli et al. | 366/130 |
| 5,766,134 A | 6/1998 | Lisak et al. | |
| 5,788,976 A | 8/1998 | Bradford | |
| 6,017,349 A | 1/2000 | Heller et al. | |
| 6,022,354 A * | 2/2000 | Mercuri et al. | 606/80 |
| 6,083,175 A | 7/2000 | Lundgren | |
| 6,387,070 B1 | 5/2002 | Marino et al. | |
| 6,468,225 B1 | 10/2002 | Lundgren | |
| 6,872,184 B2 | 3/2005 | Brannon | |
| 7,008,394 B2 | 3/2006 | Geise et al. | |
| 7,204,810 B2 | 4/2007 | Hynes et al. | |
| 7,214,059 B2 | 5/2007 | Takahashi | |
| 2003/0075564 A1 | 4/2003 | Wahlig et al. | |
| 2003/0130594 A1* | 7/2003 | Hynes et al. | 600/562 |
| 2004/0115590 A1 | 6/2004 | Takahashi | |
| 2005/0267503 A1 | 12/2005 | Hunstad | |
| 2006/0018799 A1 | 1/2006 | Wong et al. | |
| 2006/0052760 A1 | 3/2006 | Batzdorf | |
| 2006/0106353 A1* | 5/2006 | Geneve et al. | 604/319 |
| 2007/0161943 A1 | 7/2007 | Lidgren et al. | |

(Continued)

FOREIGN PATENT DOCUMENTS

EP 0 758 551 A1 2/1997

(Continued)

*Primary Examiner*—Michele Kidwell

(57) ABSTRACT

A collection device for collecting bone material during a spinal fusion surgical procedure so that the bone material can later be used as a graft material for the fusion procedure. The device includes a container that collects the bone and other material that is removed from the patient during the surgical procedure through a suction hose. The device includes a plunger having a filter plate sealed to the inside of the container. The plunger is pushed down into the collected material in the container so that blood and other liquids are forced through the plate to be separated from the bone material. A cover at the bottom of the container can be removed to remove the collected bone material.

27 Claims, 6 Drawing Sheets

U.S. PATENT DOCUMENTS

2007/0203471 A1    8/2007   Anspach et al.

FOREIGN PATENT DOCUMENTS

| WO | WO 00/45713 A1 | 8/2000 |
| WO | WO 2006/027565 A1 | 3/2006 |
| WO | WO 2006/100651 A1 | 9/2006 |
| WO | WO 2007/053918 A1 | 5/2007 |

* cited by examiner

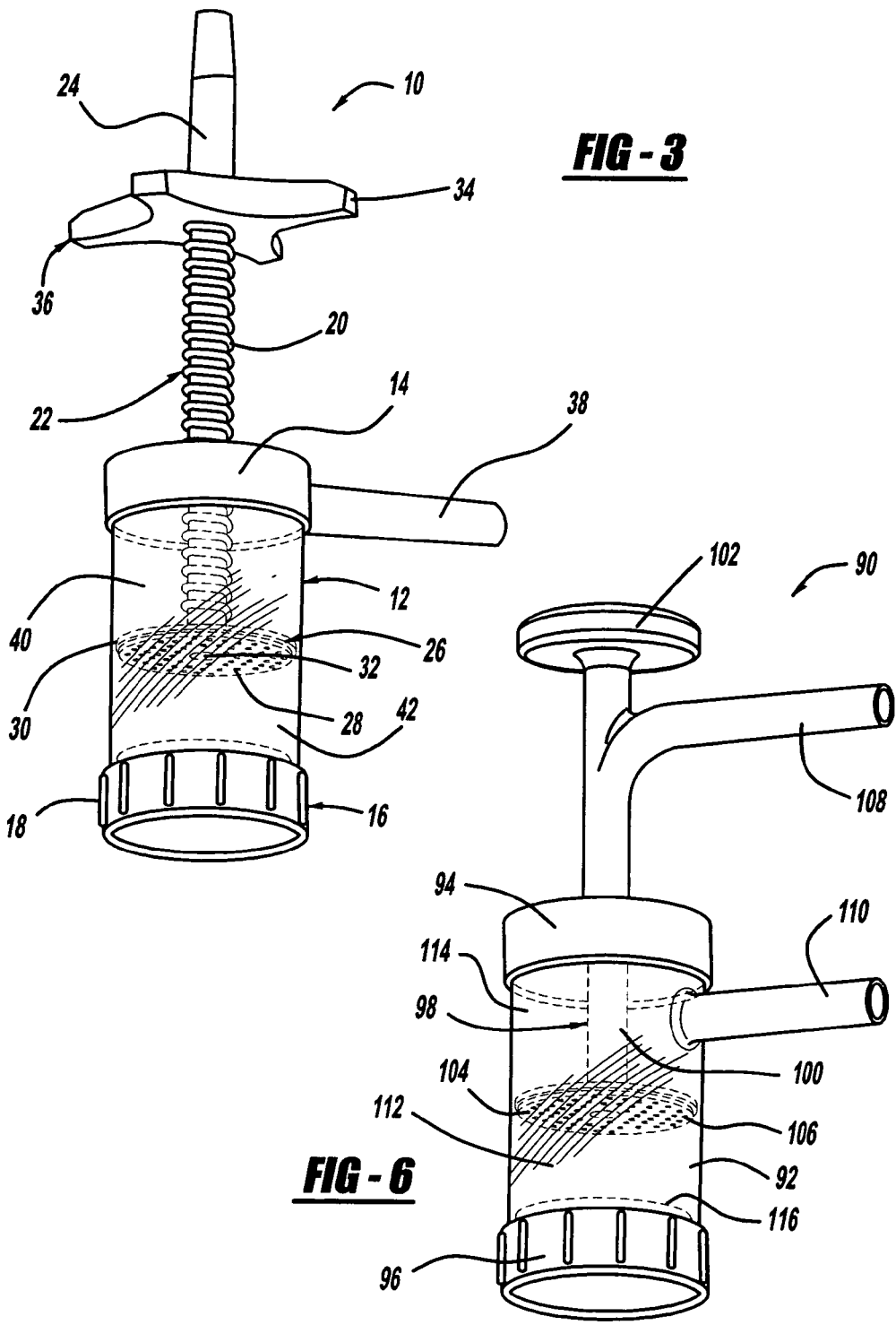

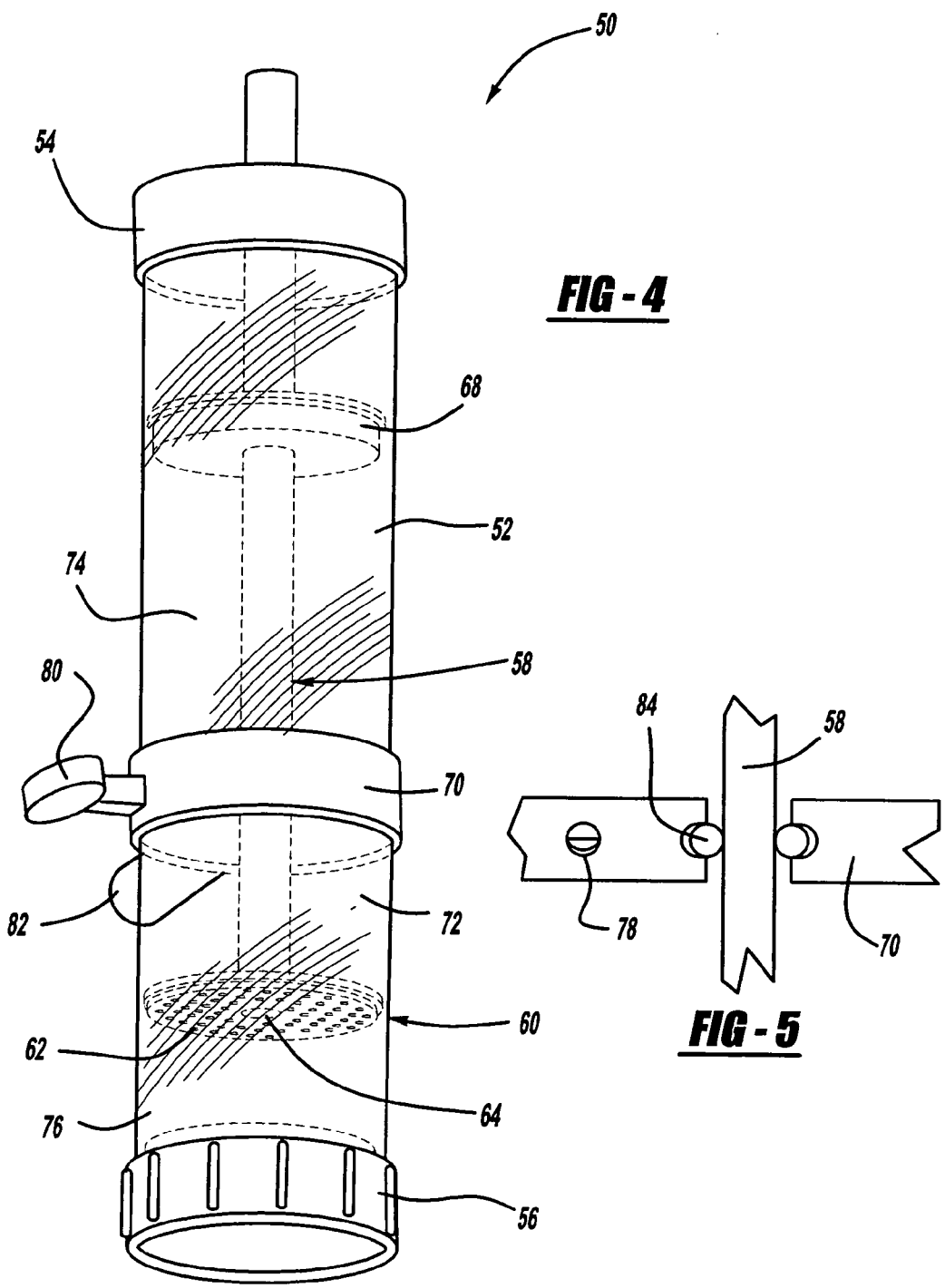

DEVICE FOR COLLECTING BONE MATERIAL DURING A SURGICAL PROCEDURE

CROSS REFERENCE TO RELATED APPLICATIONS

This application claims the benefit of the priority date of U.S. Provisional Patent Application No. 60/785,060, titled Device for Collecting Bone Material During a Surgical Procedure, filed Mar. 23, 2006.

BACKGROUND OF THE INVENTION

1. Field of the Invention

This invention relates generally to a device for collecting bone material during a surgical procedure and, more particularly, to a device for collecting bone material during spinal fusion surgery that includes a filter for separating blood and other liquid matter from the collected material so that the separated bone material can be used as graft material for spinal fusion.

2. Discussion of the Related Art

The human spine includes a series of vertebrae interconnected by connective tissue referred to as disks that act as a cushion between the vertebrae. The disks allow for movement of the vertebrae so that the back can bend and rotate.

Spinal fusion is a surgical procedure that fuses two or more vertebrae together using bone grafts and/or other devices. Spinal fusion is a commonly performed procedure for the treatment of chronic neck and back pain refractory to non-operative treatments. Spinal fusion is used to stabilize or eliminate motion of vertebrae segments that may be unstable, i.e., move in an abnormal way, that may lead to pain and discomfort. Spinal fusion is typically performed to treat injuries to the vertebrae, degeneration of the spinal disks, abnormal spinal curvature and a weak or unstable spine.

Spinal fusion generally requires a graft material, usually bone material, to fuse the vertebrae together. The bone graft material can be placed over the spine to fuse adjacent vertebrae together. Alternatively, a cage is positioned between the vertebrae being fused, and is filed with the graft material. The cage includes holes that allow the vertebrae and the graft material to grow together to provide the fusion. The cage supports the weight of adjacent vertebrae while the fusion is occurring through the cage. Typically the bone graft material is autogenous bone material taken from the patient, or allograft bone material harvested from cadavers. Synthetic bone materials can also be used as the graft material. Generally, the patient's own bone material offers the best fusion material and is the current "gold standard".

Known bone fusion materials include an iliac crest harvest from the patient, bone graft extenders, such as hydroxyapetite and demineralized bone matrix, and bone morphogenic protein. However, using these materials provides a number of disadvantages. Autologous graft harvest is associated with increased operative and anesthetic time, increased blood loss, increased patient discomfort and increased hospital stay. Iliac crest harvest includes complications and post-operative pain, and is associated with a 15% complication rate. Further, iliac crest harvest can be complicated by wound hematomas and infections, neuropraxias and chronic pain, iliac fractures and bowel injuries. Also, iliac crest graft harvest is painful and makes early ambulation difficult. Bone graft extenders are expensive, are not the patient's own bone, often dissolve and often do not form good bone material when used alone. Some studies have shown complete resolution of these substrates without bone formation despite their touted benefits by industry. Bone morphogenic protein, though shown to be effective at bone formation, is extremely expensive, and can lead to complications, such as soft-tissue swelling, bone formation in places that it should not be, etc. Further, bone morphogenic protein is a poor graft material for posterolateral fusions.

During most spinal surgical procedures, a drill is used to take bone away to allow for decompression of the spinal nerves and/or the spinal cord. Bone is also drilled from the spine to create a "decorticated" fusion bed. Typically, this bone is removed by suction and transported into a large trap outside the surgical field along with the blood and irrigation solution. The collected material is then discarded as surgical waste.

SUMMARY OF THE INVENTION

In accordance with the teachings of the present invention, a collection device for collecting bone material during a spinal fusion surgical procedure is disclosed so that the bone material can later be used as a graft material for the fusion procedure. The device includes a container that collects the bone and blood that is removed from the patient through a suction hose during the surgical procedure. The device includes a plunger having a filter plate sealed to the inside of the container that allows liquid to flow therethrough. The plunger is pushed down into the collected material in the container so that blood and other liquids are forced through the filter plate to be separated from the bone material. An outgoing suction line is used to suck out the separated blood from the container after is permeates through the plate. A cover at the bottom of the container can be removed to remove the collected bone material.

Additional features of the present invention will become apparent from the following description and appended claims, taken in conjunction with the accompanying drawings.

BRIEF DESCRIPTION OF THE DRAWING

FIG. 3 is a perspective view of a collection device for collecting bone material during a spinal fusion surgical procedure, according to an embodiment of the present invention;

FIG. 4 is a perspective view of a collection device for collecting bone material during a spinal fusion surgical procedure, according to another embodiment of the present invention;

FIG. 5 is a broken-away, cross-sectional view of a plate in the collection device shown in FIG. 4 including a valve for directing suction to different chambers within the collection device;

FIG. 6 is a perspective view and FIG. 7 is a cross-sectional view of a collection device for collecting bone material during a spinal fusion surgical procedure, according to another embodiment of the present invention;

DETAILED DESCRIPTION OF THE EMBODIMENTS

The following discussion of the embodiments of the invention directed to a collection device for collecting bone material during a surgical procedure is merely exemplary in nature, and is in no way intended to limit the invention or its applications or uses. For example, the collection device of the invention has particular application for collecting bone graft material that is generated by drilling and collecting by suctioning the surgical field during a spinal fusion procedure. However, as will be appreciated by those skilled in the art, the collection device of the invention may have application for other surgical procedures, such as various orthopedic procedures, such as cranio-facial surgical procedures, long bone non-union surgical procedures, etc.

Figure 1:
FIG. 1 is an H and E stained microscopic image of bone material removed through a suction trap from a patient during a spinal fusion surgical procedure.

One of the present inventors has performed research and experimentation into the feasibility of using bone material collected during a spinal fusion surgical procedure as part of the fusion material. Particularly, the present inventor has proposed using a Luken sputum trap to collect bone material as it is being removed from the spine during a spinal fusion procedure. Analysis of the bone material collected in the sputum trap has shown that it includes osteogenic bone cells that are particularly suitable for spinal grafts. An H and E stained microscopic image of bone material removed through a suction trap during a spinal fusion surgery is shown in FIG. 1 illustrating the quality of the collected bone material. The sputum trap is coupled to a suction tube used to draw material away from the spine as the bone is being drilled for decompression of the nerves or spinal cord. Typically this material is thrown away yet if properly collected it has been discovered that the bone material is an excellent fusion material, providing all the components needed to form healthy bone, i.e., osteogenic, osteoconductive, and osteoinductive material. However, because bone is vascularized, the sputum trap also collects blood which needs to be filtered out.

Once the material is collected in the sputum trap, saline can be added to the mixture to wash the bone dust to remove excess blood. A sponge can be used to filter out the blood from the trap and leave the bone dust behind. Suction can be used in combination with the sponge to suck out the washed blood leaving a plug of the bone material behind in the trap. The bone material that is left behind can then be mixed with other material, such as bone graft extenders, to provide additional graft material as required for fusion. Thus, the bone material can be used alone or extend the usefulness and ability of graft extenders to achieve fusion since it contains the cells that promote healthy bone formation. Additional benefits include no need for additional bone harvest, namely from the iliac crest, reusing the bone removed from the spine, and generating graft material containing viable autologous bone cells.

Figure 2:
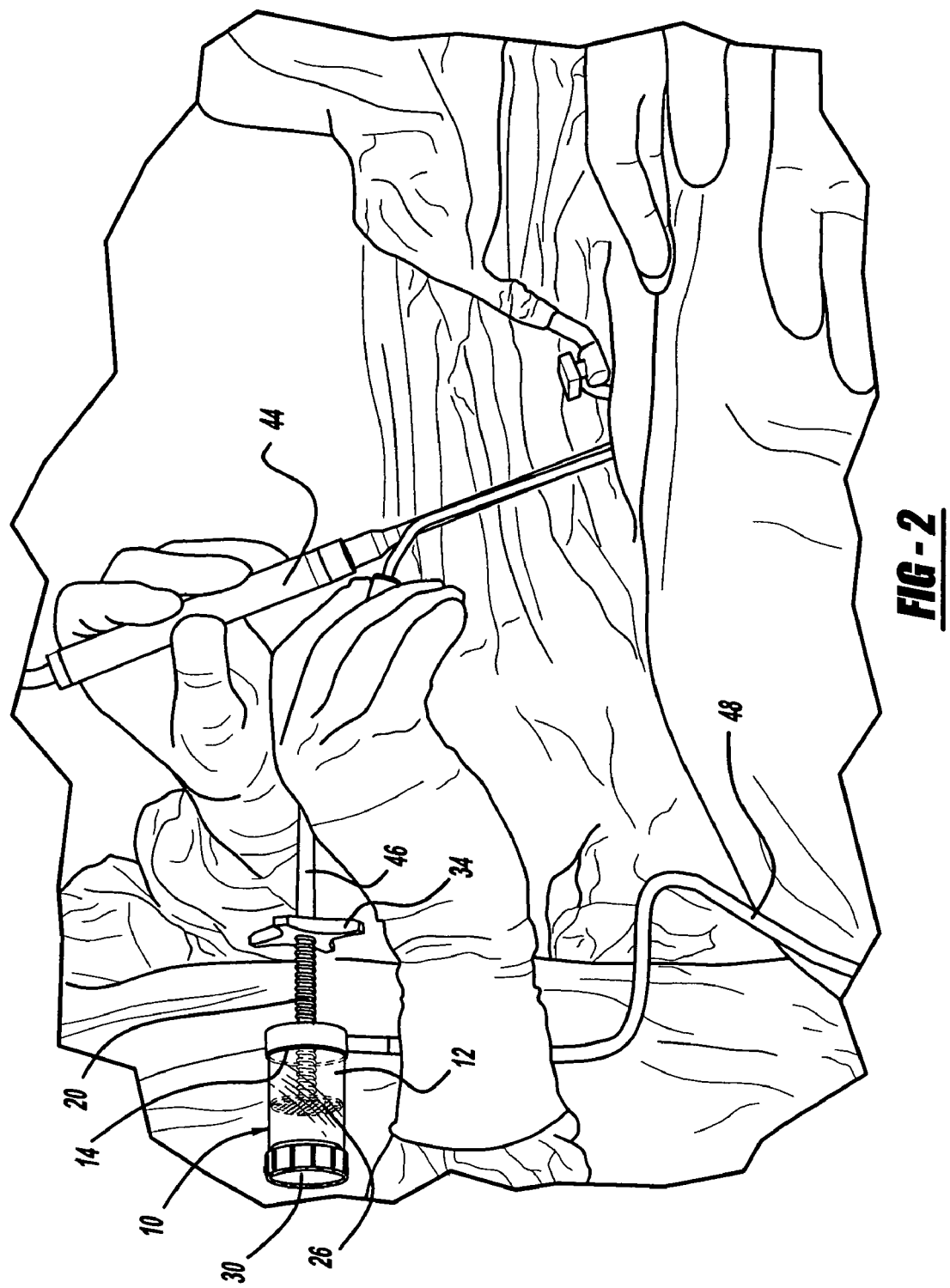
FIG. 2 is an illustration of a surgeon performing a spinal fusion surgical material and collecting bone material in a collection device, according to an embodiment of the present invention.

FIG. 2 is an illustration of a surgeon performing a spinal fusion surgical procedure on a patient through a tubular retractor. The surgeon is using a drilling device 44 to remove bone while performing a fusion procedure between adjacent vertebrae. During the cleaning process, bone material is removed from the vertebras. Suction is used to remove the drilled material from the surgical field. According to the invention, a collection device 10 is used to collect the bone material as it is drilled from the surgical field. An input suction line 46 is coupled to the drilling device 44 and the collection device 10. An output suction line 48 is coupled to the collection device 10 and a suction pump (not shown). The pump provides the suction that draws the drilled material from the surgical field through the input suction line 46 and into the collection device 10, as will be discussed in more detail below.

FIG. 3 is a perspective view of the collection device 10 for collecting bone material during a spinal fusion surgical procedure, according to an embodiment of the present invention. The device 10 includes a cylindrical collection container 12 having a top cover 14 and a bottom cover 16. For reasons that will become apparent from the discussion below, the bottom cover 16 is threadable to the container 12 or is coupled thereto in a friction fit so that it can be easily removed. The bottom cover 16 includes ridges 18 that allow the surgeon to quickly and effectively remove the bottom cover 16 when desired. In one non-limiting embodiment, the container 12 is made of a suitable clear durable plastic, and the other parts of the device 10 are made of a suitable durable plastic.

The device 10 further includes a plunger 22 having a rod 24 with a bore extending therethrough, where the rod 24 includes a threaded portion 20. The plunger 22 further includes a filter plate 26 positioned within the container 12, where the plate 26 separates the container 12 into an upper chamber 40 and a lower chamber 42. The filter plate 26 includes an array of pores or holes 28 extending therethrough. The holes can be all the same diameter or different diameters. In one non-limiting embodiment, the size of the holes 28 can be about 0.33 mm. However, other pore sizes may be equally applicable for the various surgical procedures. Further, the filter plate 26 can include a suitable membrane instead of a plate with holes that allows liquids to pass therethrough. In this embodiment, the membrane would be very thin, and may require a backing plate for support.

The plate 26 also includes an outer O-ring 30 positioned against the inside wall of the container 12 to provide a seal between the plate 26 and the container 12, and allow the filter plate 26 to be moved smoothly within the container 12. The plate 26 also includes a central opening 32 that is in fluid communication with the bore extending through the rod 24. The plunger 22 further includes a handle 36 rigidly secured to the rod 24 that is rotated to thread the threadable portion 20 through a threaded opening in the top cover 14 so that the filter plate 26 can be moved up and down in the container 12. The handle 36 includes extended tabs 34 that allow the surgeon to easily grasp the handle 36. A suction port 38 is in fluid communication with the upper chamber 40 of the container 12, and can be integral with the top cover 14 or a top portion of the chamber 40.

During the surgical procedure, the open end of the rod 24 is connected to the input suction line 46 and the suction port 38 is connected to the output suction line 48 that is coupled to the pump. The input suction line 46 can include a hand-held sucker or other surgical device. In an alternate embodiment, the rod 24 and the suction line 46 are integral with each other, where the collection device 10 is coupled directly to the drilling device 44. The size of the collection device 10 may be reduced so that it is part of the drilling device 44, or other device, that is held by the surgeon. The surgeon will position the filter plate 26 at a desirable position within the container 12 so that the lower chamber 42 is the proper size for the particular procedure. As the surgeon cuts and drills away material between the vertebrae being fused, the hand-held sucker is used to draw away the removed bone, blood and other material from the surgical area. That material is sucked into the container 12 through the bore in the rod 24 and the opening 32 so that it is collected in the lower chamber 42 of the container 12. The blood and other liquid material will be sucked into the upper chamber 40 through the holes 28 and out of the container 12 through the suction port 38. The size and number of the holes 28 are selected so that the blood will be able to flow therethrough, and the bone material will not.

The collection device 10 can be positioned within a stand (not shown) to hold it upright so that it does not tip causing bone and blood material from being sucked out of the suction port 38. Further, the bore in the rod 24 can be plugged with some device when the filter plate 26 is moved against the collected material so that the collected material does not go up the inlet port.

After the surgical area is prepared and the material is removed from the area, the surgeon will then need to fuse the vertebrae together using a graft material. According to the invention, the graft material includes collected bone material in the container 12. The surgeon will use the handle 36 to move the filter plate 26 farther into the container 12 against the collected material. Blood and other liquids in the collected material will be squeezed through the array of holes 28. The separated blood is removed from the upper chamber 40 of the container 12 through the suction port 38. Saline can be mixed in with the remaining material in the lower chamber 42 to wash away more of the blood from the bone material. The surgeon will then remove the bottom cover 16 to collect the bone material from the container 12 and use it as the graft material to fuse the vertebrae together.

FIG. 4 is a perspective view of a collection device 50 including a cylindrical container 52, according to another embodiment of the present invention. In this embodiment, the container 52 is longer than the container 12. The container 52 includes a top cover 54 and a bottom cover 56 of the type discussed above. Further, the collection device 50 includes a plunger 58 having a filter plate 60 with holes 62 and a central opening 64 similar to the filter plate 26. In this embodiment, the plunger 58 also includes a pressure plate 68 and a separator plate 70 that define a first chamber 72 between the filter plate 60 and the separator plate 70 and a second chamber 74 between the filter plate 60 and the pressure plate 68. A collection chamber 76 is provided between the filter plate 60 and the bottom cover 56. The bone material is collected in the collection chamber 76, and is removed through the bottom of the container 52 in the manner as discussed above.

FIG. 5 is a broken-away, cross-sectional view of the separator plate 70. The separator plate 70 includes a valve 78 whose position is controlled by a knob 80. The valve 78 is turned to one position by the knob 80 so that suction from an output port 82 removes material from the chamber 72 during the surgical procedure. When it is time to remove the collected material from the chamber 76, the valve 78 is moved to the other position so that suction is applied to the chamber 74 to pull the pressure plate 68 down towards the filter plate 60 to provide the pressure required to press the collected material so that the liquid in the collection chamber 76 is forced into the chamber 72. The valve 78 can then be turned back to remove the liquid from the chamber 72. Thus, manual operation is not required to press the collected material in the collection chamber 76.

Figure 7:
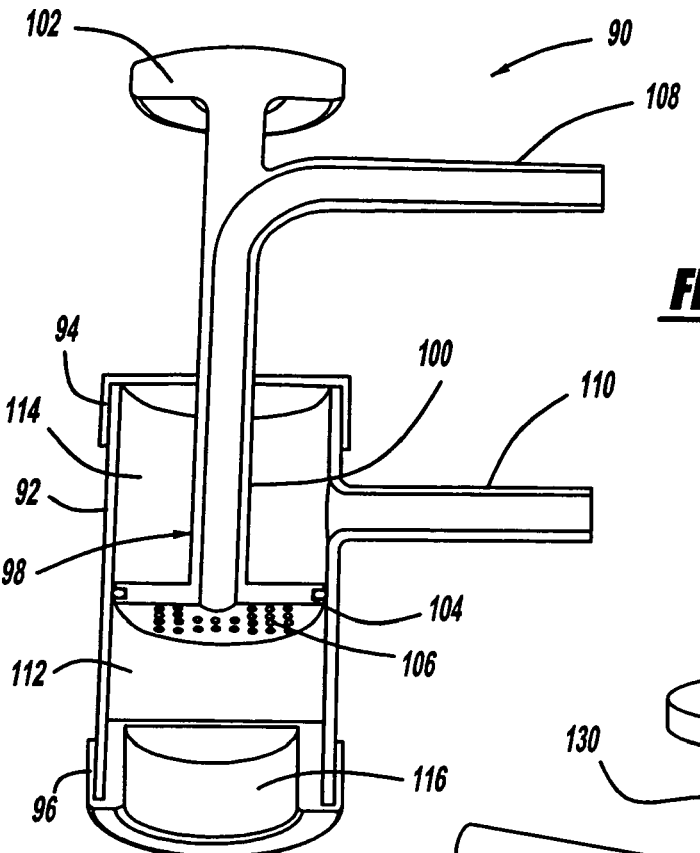

FIG. 6 is a perspective view and FIG. 7 is a cross-sectional view of a collection device 90 for collecting bone material during a spinal fusion procedure, according to another embodiment of the present invention. In this embodiment, the device 90 includes a container 92 having a top cover 94 and a bottom cover 96 similar to the top and bottom covers discussed above. Further, the device 90 includes a plunger 98 having a plunger rod 100 with a circular handle 102. The plunger 98 further includes a filter plate 104 having an array of holes 106 extending therethrough. In this embodiment, an inlet suction port 108 is coupled to the rod 100 between the handle 102 and the top cover 84, and is in fluid communication with a lower chamber 112 of the container 92 through a bore in the plunger rod 100. An outlet suction port 110 is coupled to the container 92, and is in fluid communication with an upper chamber 114 of the container 92. The handle 102 is used to push the filter plate 104 into the collected material in the lower chamber 112 for the purposes discussed above. The collection device 90 also includes a cup 116 attached to the bottom cover 96 for collecting the bone material.

Figure 8:
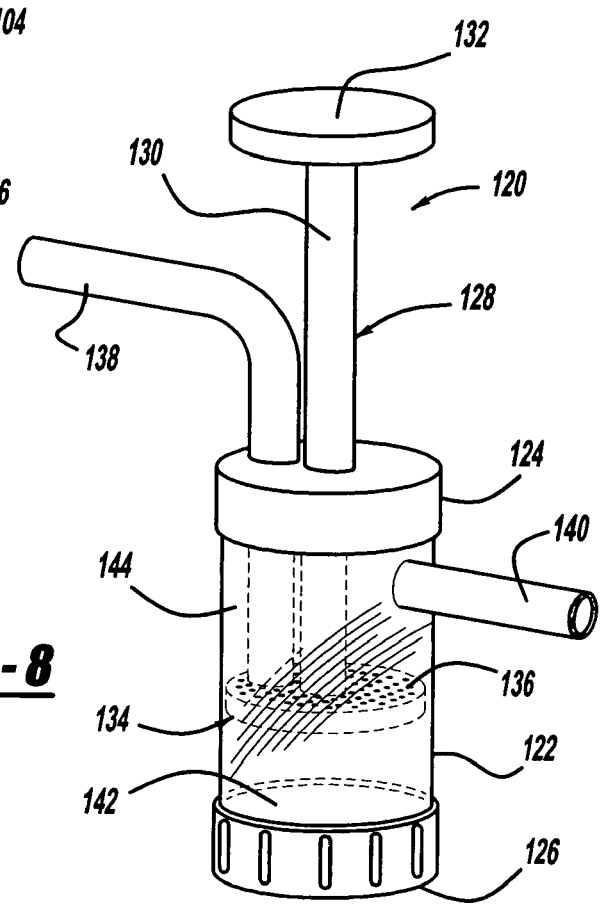
FIG. 8 is a perspective view of a collection device for collecting bone material during a spinal fusion surgical procedure, according to another embodiment of the present invention.

FIG. 8 is a perspective view of a collection device 120 for collecting bone material during a spinal fusion procedure, according to another embodiment of the present invention. In this embodiment, the device 120 includes a container 122 having a top cover 124 and a bottom cover 126 similar to the top and bottom covers discussed above. Further, the device 120 includes a plunger 128 having a plunger rod 130 with a circular handle 132. The plunger 128 further includes a filter plate 134 having an array of holes 136 extending therethrough. In this embodiment, an inlet suction port 138 extends through the top cover 124 into the container 122 and is coupled to the filter plate 134, as shown. The inlet suction port 138 is in fluid communication with a lower chamber 142 of the container 122 through a hole in the filter plate 134. An outlet suction port 140 is coupled to the container 122, and is in fluid communication with an upper chamber 144 of the container 122. The handle 132 is used to push the filter plate 134 into the collected material in the lower chamber 142 for the purposes discussed above.

Figure 9:
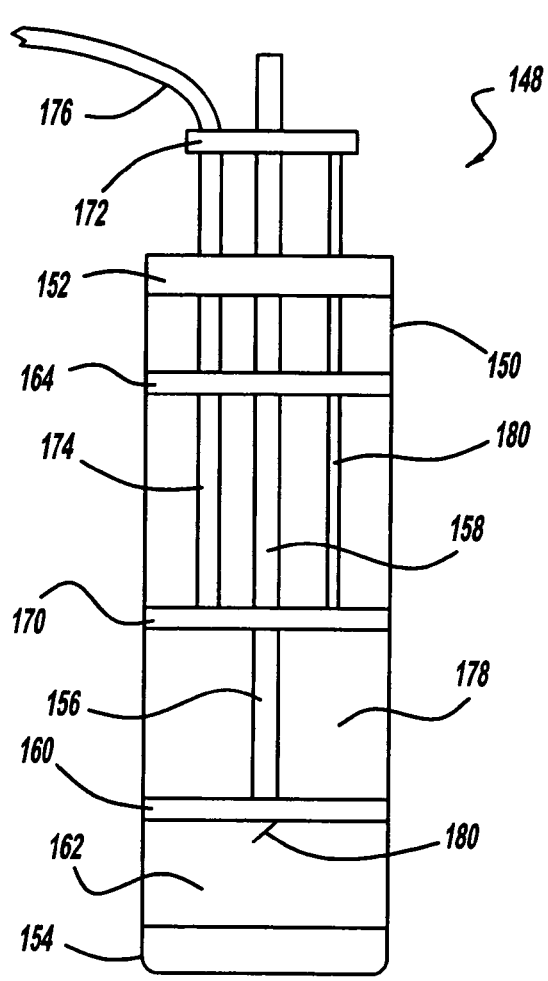
FIG. 9 is a side view and FIG. 10 is a top view of a collection device for collecting bone material during a spinal fusion surgical procedure, according to another embodiment of the present invention.
Figure 10:
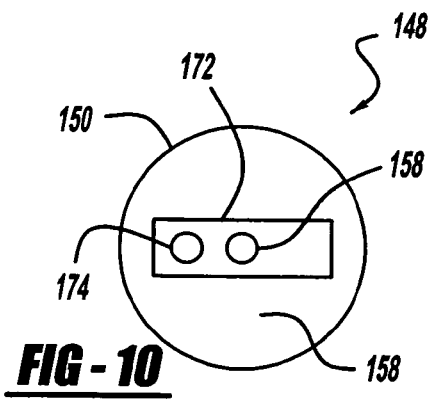

FIG. 9 is a side view and FIG. 10 is a top view of a collection device 148 including a container 150 for collecting bone material, according to another embodiment of the present invention. The collection device 148 includes a top cover 152 and a bottom cover 154 of the type discussed above. Further, the collection device 148 includes a plunger 156 having a rod 158 and a filter plate 160 attached thereto of the type discussed above. The rod 158 is hollow and acts as an inlet line where the blood and bone material is collected in a collection chamber 162 between the filter plate 160 and the bottom cover 154. Additionally, the plunger 156 includes a stabilizing plate 164 that is rigidly secured to the rod 158. A flap 180 is used to cover the opening of the rod when the plunger 156 is being pushed into the collective material. This prevents blood and other liquids from going up the rod 158 and subsequently still being trapped within the collected material. The flap 180 can be attached to the filter plate 160 in any suitable technique so that it is hinged, and will open when material is being put into the container 150 through the rod 158. In one embodiment, the flap 180 is ultrasonically welded to the filter plate 160. In an alternate embodiment, a check valve or flapper valve can be positioned within the rod 158 at a suitable location so that fluid and other material is allowed to flow into the chamber 162 through the rod 158, but is prevented from flowing into the rod 158 from the chamber 162. The flap 180 is intended to represent any suitable device that provides this operation.

According to this embodiment of the invention, a separator plate 170 is slidably movable within the container 150 to change the working volume of the container 150 for different surgical procedures. A handle 172 is provided to move the separator plate 170 within the container 150 independent of the plunger 156. A hollow tube 174 is rigidly coupled to the handle 172 and the separator plate 170, where an open end of the tube 174 through the handle 172 can be attached to an outlet line 176. Further, the other end of the hollow tube 174 is in fluid communication with a chamber 178, and allows material collected in the chamber 178 to be sucked out of the container 150 through the outlet line 176.

A stabilizing rod 180 is rigidly coupled to the handle 172 and the separator plate 170. The tube 174 and the rod 180 are slidably coupled to the stabilizing plate 164 and the top cover 152 in a sealed manner. By lifting up and pulling down on the handle 172, the separator plate 170 can be positioned at a desirable location within the container 150 to adjust the size of the chamber 178. Additionally, the rod 158 is slidably coupled to the separator plate 170 so that when the filter plate 160 is moved up and down in the container 160, both the size of the chambers 162 and 178 are changed. Therefore, by calibrating the position of the stabilizing plate 164, the length of the container 150 and the length of the rod 158, the size of the combination of the chambers 162 and 178 can be changed through a predetermined range for different procedures.

Figure 11:
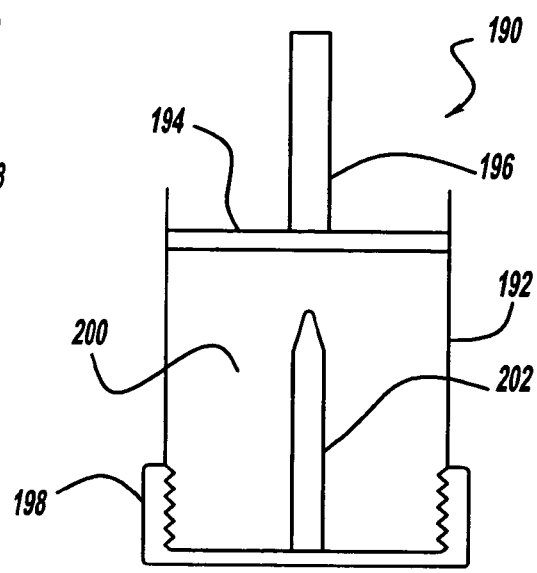
FIG. 11 is a partial cross-sectional view of a collection device for collecting bone material during a spinal fusion surgical procedure that includes a closing spike for closing an inlet tube, according to another embodiment of the present invention.

FIG. 11 is a cross-sectional view of a portion of a collection device 190 including a container 192, according to another embodiment of the present invention. The collection device 190 includes a filter plate 194 and an inlet tube 196 coupled thereto for the reasons discussed above. A bottom cover 198 closes the container 192. When the filter plate 194 is pushed towards the bottom cover 198 to remove the blood from chamber 200 in the manner as discussed above, it is desirable that a minimal amount of the blood material be pushed back up into the inlet tube 196. According to this embodiment of the present invention, a closing spike 202 is rigidly coupled to the bottom cover 198 so that as the filter plate 194 is moved downward, the closing spike 202 enters the bore of the inlet tube 196 in a tight coupling within the tolerances of the collection device 190. Therefore, a limited amount of blood will back up into the inlet tube 196.

Figure 12:
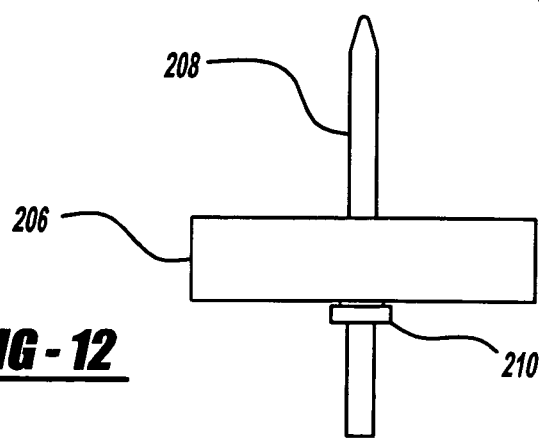
FIG. 12 is a side view of a bottom cover and adjustable closing spike for a collection device for collecting bone material during a spinal fusion surgical procedure, according to another embodiment of the present invention.

In another embodiment, the length of the closing spike 202 can be adjusted. FIG. 12 is a side view of a bottom cover 206 and a closing spike 208 slidably coupled thereto that can replace the closing spike 202 and the bottom cover 198. Once the surgeon has collected the blood and bone material in the chamber 200, he can unlock a sealed locking nut 210, and slide the closing spike 208 upward so that it is inserted into the inlet tube 196 before the filter plate 194 is pushed downward. The surgeon can position the container 192 in any desirable orientation so that material does not leak from the bottom cover 206 during this procedure. Once the closing spike 208 is in place, the surgeon can tighten the locking nut 210 to hold the spike 208 in place as the filter plate 194 is moved downward to remove the blood.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A collection device comprising:
a container including a top cover and a bottom cover;
a rod extending through the top cover and into the container;
a filter plate coupled to the rod and positioned within the container in contact therewith, wherein the rod is operable to be moved within the container so that liquid material between the filter plate and the bottom cover is forced through the filter plate and solid material is left within the container between the filter plate and the bottom cover;
an outlet suction port in fluid communication with the container between the top cover and the filter plate, said outlet suction port being operable to remove the liquid material from the container that flows through the filter plate; and
an inlet suction port in fluid communication with the container between the filter plate and the bottom cover, said inlet suction port being operable to deposit the liquid and solid material into the container between the filter plate and the bottom cover.

2. The collection device according to claim 1 wherein the inlet suction port extends through a bore in the rod and an opening in the filter plate.

3. The collection device according to claim 2 further comprising a one-way valve device, said one-way valve device allowing liquid and other material to flow through the bore in the rod into the container between the filter plate and the bottom cover, and preventing the liquid and other material from flowing from the container between the filter plate and the bottom cover into the bore.

4. The collection device according to claim 1 further comprising a handle, said rod including a threaded portion, wherein the handle is used to rotate the rod to thread it into the container through the top cover to move the filter plate.

5. The collection device according to claim 1 wherein the rod includes a push plate for pushing the filter plate into the container.

6. The collection device according to claim 1 wherein the bottom cover is removable from the container to remove material from the container.

7. The collection device according to claim 1 further comprising an outlet tube, a separator plate and a pressure plate coupled to the rod between the top cover and the filter plate, said filter plate and said separator plate defining a first chamber and said separator plate and said pressure plate defining a second chamber, said separator plate including a valve coupled to the outlet tube, wherein a first position of the valve allows suction through the outlet tube to be provided to the first chamber and a second position of the valve allows suction through the outlet tube to be provided to the second chamber to move the filter plate and force the liquid therethrough.

8. The collection device according to claim 1 further comprising a separator plate positioned between the top cover and the filter plate, said separator plate being movable to set a working volume within the container, said rod being operable to move through a central opening in the separator plate.

9. The collection device according to claim 8 further comprising an outlet tube positioned on one side of the rod and a stabilizing shaft being positioned on an opposite side of the rod, wherein the outlet tube is in fluid communication with a chamber between the separator plate and the filter plate, said container further including a plate handle having a central opening through which the rod extends.

10. The collection device according to claim 1 further comprising a closing spike rigidly coupled to the bottom cover and extending into the container, said closing spike being operable to be inserted into the rod.

11. The collection device according to claim 10 wherein the closing spike is slidably adjustable relative to the bottom cover so that it can be inserted into the rod.

12. The collection device according to claim 1 wherein the filter plate includes a plurality of holes through which the liquid flows through.

13. The collection device according to claim 1 wherein the filter plate includes a membrane through which the liquid flows.

14. The collection device according to claim 1 wherein the filter plate includes an O-ring that seals the filter plate to an inside wall of the container.

15. The collection device according to claim 1 wherein the device is a surgical device for collecting bone material during spinal fusion surgery, said filter plate separating blood as the liquid material from the bone material that is the solid material.

16. A collection device comprising:
a container including a top cover and a bottom cover;
a rod extending through the top cover and into the container;
a filter plate coupled to the rod and positioned within the container in contact therewith, wherein the rod is operable to be moved within the container so that liquid material between the filter plate and the bottom cover can be forced through the filter plate; and
an outlet tube, a separator plate and a pressure plate coupled to the rod between the top cover and the filter plate, said filter plate and said separator plate defining a first chamber and said separator plate and said pressure plate defining a second chamber, said separator plate including a valve coupled to the outlet tube, wherein a first position of the valve allows suction through the outlet tube to be provided to the first chamber and a second position of the valve allows suction through the outlet tube to be provided to the second chamber to move the filter plate and force the liquid therethrough.

17. The collection device according to claim 16 further comprising an outlet suction port in fluid communication with the container between the top cover and the filter plate, said outlet suction port being operable to remove the liquid material from the container that flows through the filter plate.

18. The collection device according to claim 16 further comprising an inlet suction port in fluid communication with the container between the filter plate and the bottom cover, said inlet suction port being operable to deposit the liquid and other material into the container between the filter plate and the bottom cover.

19. The collection device according to claim 18 wherein the inlet suction port extends through a bore in the rod and an opening in the filter plate.

20. The collection device according to claim 16 wherein the bottom cover is removable from the container to remove material from the container.

21. The collection device according to claim 16 wherein the device is a surgical device for collecting bone material during spinal fusion surgery, said filter plate separating blood from the bone material.

22. A collection device comprising:
a container including a top cover and a bottom cover;
a rod extending through the top cover and into the container;
a filter plate coupled to the rod and positioned within the container in contact therewith, wherein the rod is operable to be moved within the container so that liquid material between the filter plate and the bottom cover can be forced through the filter plate;
a separator plate positioned between the top cover and the filter plate, said separator plate being movable to set a working volume within the container, said rod being operable to move through a central opening in the separator plate; and
an outlet tube positioned on one side of the rod and a stabilizing shaft being positioned on an opposite side of the rod, wherein the outlet tube is in fluid communication with a chamber between the separator plate and the filter plate, said container further including a plate handle having a central opening through which the rod extends.

23. The collection device according to claim 22 further comprising an outlet suction port in fluid communication with the container between the top cover and the filter plate, said outlet suction port being operable to remove the liquid material from the container that flows through the filter plate.

24. The collection device according to claim 22 further comprising an inlet suction port in fluid communication with the container between the filter plate and the bottom cover, said inlet suction port being operable to deposit the liquid and other material into the container between the filter plate and the bottom cover.

25. The collection device according to claim 24 wherein the inlet suction port extends through a bore in the rod and an opening in the filter plate.

26. The collection device according to claim 22 wherein the bottom cover is removable from the container to remove material from the container.

27. The collection device according to claim 22 wherein the device is a surgical device for collecting bone material during spinal fusion surgery, said filter plate separating blood from the bone material.

* * * * *